United States Patent [19]

Goerner et al.

[11] Patent Number: 4,692,544

[45] Date of Patent: Sep. 8, 1987

[54] INHIBITING POLYMERIZATION OF ETHYLENICALLY UNSATURATED MONOMERS

[75] Inventors: Richard N. Goerner, Mount Holly; J. Michael Hipp; Ruth H. Hipp, both Iron Station, all of N.C.

[73] Assignee: Sandoz Ltd., Basel, Switzerland

[21] Appl. No.: 768,709

[22] Filed: Aug. 23, 1985

[51] Int. Cl.[4] .................. C07C 69/54; C07C 69/56; C07C 7/20; C07C 29/94; C07C 51/50; C07C 85/26; C07C 121/30

[52] U.S. Cl. .................. 560/4; 260/398.5; 260/544; 260/546; 558/306; 560/2; 560/3; 562/598; 564/4; 568/701; 585/2; 585/5

[58] Field of Search .................. 260/465.9, 398.5, 544, 260/546; 564/4; 558/306; 585/2, 5; 560/2, 3, 4; 562/598; 568/701

[56] References Cited

U.S. PATENT DOCUMENTS

| | | | |
|---|---|---|---|
| 3,230,225 | 1/1966 | Arrigo | 560/4 X |
| 3,426,063 | 2/1969 | Gros | 560/4 X |
| 3,696,050 | 10/1972 | Werts et al. | 252/403 |
| 3,715,386 | 2/1973 | Sherr | 560/4 |
| 3,855,281 | 12/1974 | Sullivan et al. | 560/4 |
| 3,959,358 | 5/1976 | Jurisch | 560/4 X |
| 4,016,198 | 4/1977 | Wilder | 560/4 |
| 4,017,544 | 4/1977 | Mullins | 560/4 |
| 4,466,905 | 8/1984 | Butler et al. | 252/403 |

*Primary Examiner*—Werren B. Lone
*Assistant Examiner*—Vera C. Clarke
*Attorney, Agent, or Firm*—Gerald D. Sharkin; Richard E. Vila; Thomas C. Doyle

[57] ABSTRACT

Certain substituted diaryl amines are used to inhibit the polymerization of ethylenically unsaturated monomers; for example, unsaturated carboxylic acids and derivatives thereof.

38 Claims, No Drawings

INHIBITING POLYMERIZATION OF ETHYLENICALLY UNSATURATED MONOMERS

This invention relates to the use of certain substituted diaryl amines to inhibit the polymerization of ethylenically unsaturated monomers.

Accordingly, the present invention provides a method for inhibiting polymerization of a polymerizable ethylenically unsaturated monomer which comprises admixing therewith a polymerization inhibiting-effective amount of a compound or mixture of compounds of formula (1)

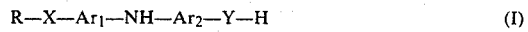
(I)

wherein

Ar$_1$ and Ar$_2$, independently, are substituted or unsubstituted aromatic ring systems, X and Y, independently, are —NH—, —S— or —O—, and R is hydrogen, substituted or unsubstituted alkyl, substituted or unsubstituted cycloalkyl, substituted or unsubstituted aryl, substituted or unsubstituted aralkyl or substituted or unsubstituted arylcycloalkyl.

The present invention also provides novel compositions comprising a polymerizable ethylenically unsaturated monomer and a polymerization inhibiting-effective amount of a compound of formula (I).

In the compounds of formula (I) Ar$_1$ and Ar$_2$ are, preferably, phenylene, naphthylene, anthrylene or phenanthrylene, which may be substituted or unsubstituted. More preferably, Ar$_1$ and Ar$_2$ are, independently, substituted or unsubstituted phenylene or naphthylene, most preferably substituted or unsubstituted phenylene.

Any substituent on Ar$_1$ and Ar$_2$ is preferably selected from those which donate electron density to the aromatic nucleus to which they are attached.

More preferably, any substituent on Ar$_1$ or Ar$_2$ is C$_{1-10}$ alkyl, phenyl, naphthyl, phenyl C$_{1-10}$ alkyl, naphthyl C$_{1-10}$ alkyl, C$_{1-10}$ alkoxy, hydroxy, C$_{1-10}$ alkylamino, amino, thiol, C$_{1-10}$ alkylthio, C$_{5-10}$ cycloalkyl, C$_{5-10}$ cycloalkyloxy or C$_{5-10}$ cycloalkylamino.

R is preferably hydrogen; substituted or unsubstituted C$_{1-10}$ alkyl; substituted or unsubstituted C$_{5-10}$ cycloalkyl; substituted or unsubstituted phenyl, naphthyl, anthryl or phenanthryl; substituted or unsubstituted phenyl C$_{1-10}$ alkyl or naphthyl C$_{1-10}$ alkyl; or substituted phenyl C$_{5-10}$ cycloalkyl or naphthyl C$_{5-10}$ cycloalkyl; with substituted or unsubstituted phenyl or naphthyl, especially substituted or unsubstituted phenyl, being the more preferred aryl significances.

Any substituent on R is preferably C$_{1-10}$ alkyl, phenyl, naphthyl, phenyl C$_{1-10}$ alkyl, naphthyl C$_{1-10}$ alkyl, C$_{1-10}$ alkoxy, hydroxy, C$_{1-10}$ alkylamino, amino, thiol, C$_{1-10}$ alkylthio, C$_{5-10}$ cycloalkyl, C$_{5-10}$ cycloalkyloxy or C$_{5-10}$ cycloalkylamino.

Any alkyl or cycloalkyl moiety in R or in a substituent on Ar$_1$ or Ar$_2$, more preferably contains 1 to 4 and 5 to 8 carbon atoms, respectively.

Preferably, Ar$_1$, Ar$_2$ and R are, independently, unsubstituted or mono- or disubstituted.

X and Y are preferably, independently, —NH— or —O—. More preferably at least one of X and Y is —NH—.

Preferably, the groups R—X— and H—Y— are para or ortho, more preferably para, with respect to the group —NH— in the center of formula (I).

A preferred class of compounds of formula (I) is that represented by formula (I')

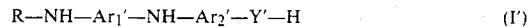
(I')

in which

R is as defined above,

Ar$_1$' and Ar$_2$' are, independently, substituted or unsubstituted phenylene or naphthylene, and Y' is —NH— or —O—.

A first more preferred subclass of compounds of formula (I') is of formula (I'a)

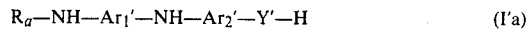
(I'a)

in which Ar$_1$', Ar$_2$' and Y' are as defined above and R$_a$ is substituted or unsubstituted phenyl.

A second more preferred subclass of compounds of formula (I') is of formula (I'b)

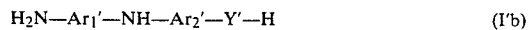
(I'b)

in which Ar$_1$', Ar$_2$' and Y' are as defined above.

In each of formulae (I'a) and (I'b), Ar$_1$' and Ar$_2$' are preferably substituted or unsubstituted phenylene, more preferably mono- or di- C$_{1-4}$ alkylphenylene or phenylene.

The most preferred compounds of formula (I'a) are those of the formula (I"a).

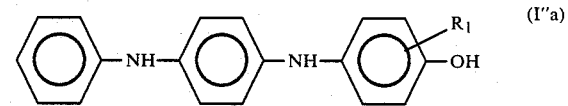
(I"a)

wherein R$_1$ is hydrogen or methyl, especially hydrogen.

The most preferred compounds of formula (I'b) are those of formula (I"b)

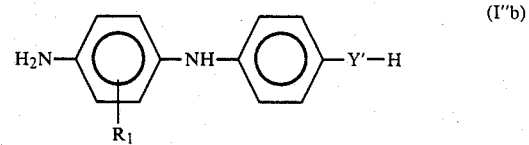
(I"b)

in which R$_1$ and Y' are as defined above, with Y' preferably being —NH—.

The compounds of formula (I) are either known or can be produced by known processes from known starting materials.

The ethylenically unsaturated monomers which can be treated in accordance with the present invention include, but are not limited to, unsaturated carboxylic acids and derivatives thereof, such as esters, anhydrides, amides and halides, as well as unsaturated nitriles. Also included are polymerizable vinyl compounds, e.g. vinyl halides, vinyl acetate, vinyl alcohol and aromatic vinyl compounds, such as styrene.

Representative of the unsaturated carboxylic acids and derivatives thereof are C$_{3-18}$ mono-, di- and tricarboxylic acids, such as acrylic, methacrylic, angelic, crotonic and oleic acids and their corresponding anhydrides, chlorides, amides and unsubstituted and substituted C$_{1-18}$ alkyl and alkenyl esters, such as methyl, ethyl, butyl, 2-ethylhexyl, lauryl, stearyl and dimethylaminoethyl esters, as well as acrylonitrile and methacrylonitrile. Preferred monomers of this type are acrylic and methacrylic acid, and the anhydrides, chlorides and $C_{1-18}$ alkyl esters thereof, especially the esters.

Representative of the vinyl compounds are vinyl chloride, vinyl acetate, vinyl alcohol, styrene, alphamethyl styrene, vinyl toluene and vinyl naphthalene, especially styrene.

The compound of formula (I) may be mixed with the monomer at any stage where it is desired to inhibit polymerization, e.g. during manufacture, purification, transportation or storage. Of particular interest is the inhibition of polymerization during distillation of the monomer and for this purpose the compound of formula (I), or a mixture thereof, may be introduced into the distillation pot, the distillation column, the condensers or ancillary equipment. Usually it is mixed with the monomer in the distillation pot.

It may also be advantageous to add some of the inhibitor of this invention to the monomer after completion of distillation in order to prevent polymerization during transportation and/or storage.

The compound of formula (I) may be added directly to the monomer without any preliminary conditioning. Preferably, however, it is first dissolved in a suitable solvent which will not interfere in any subsequent treatment of the monomer. An especially suitable solvent is the monomer itself. However, other solvents may include components used in the preparation of the monomer, such as alcoholic or olefinic components, and other inert solvents appropriate to the processing step at which the application will occur.

The amount of polymerization inhibitor will depend on the particular monomer and the conditions under which polymerization is to be inhibited. It will be well within the skill of the art to determine, without undue experimentation, what amounts are suitable for a given monomer and set of conditions, especially temperature. While, as indicated hereinafter, an amount of 10 parts per million (0.001%) based on the weight of the monomer has been found to be effective, it is contemplated that in normal useage higher concentrations will be employed. In general, the amount of compound of formula (I) can range from as little as 0.0005% by weight, based on the weight of the monomer, up to the solubility limit of the compound, e.g. about 20% in methyl methacrylate. The preferred range is about 0.001 to 5%, more preferably 0.01 to 0.5%, by weight.

When it is desired to polymerize the monomer, any of the inhibitor which is still in contact therewith can be separated by distillation or by other conventional methods, e.g. solvent extraction. On the other hand, small amounts of the inhibitor may not require removal but may instead be counteracted by the use of an effective amount of polymerization initiator.

The following describe testing which has been carried out for the purpose of evaluating the polymerization inhibition according to the present invention.

Inhibition Testing

The inhibitor to be evaluated was dissolved in freshly distilled (inhibitor-free) methyl methacrylate monomer to a concentration of 10 ppm (0.001%), by weight. Samples (10 ml each) of the resulting test solution were pipetted into individual test tubes which were then sparged with nitrogen to displace dissolved oxygen. Each sample was sealed under a nitrogen blanket with a closure containing a thermocouple enclosed in a glass sheath (containing silicon oil) which protruded into the test solution. A control sample was prepared in the identical manner, except that no inhibitor was added to the methyl methacrylate.

The tubes containing the test solution and the control were then placed in a thermostatically controlled oil bath preheated to a test temperature of 90° C. The thermocouples were connected to an Esterline Angus datalogger programmed to collect and record time and temperature data at fifteen minute intervals.

When polymerization occurred, the heat given off caused a rise in temperature which was sensed by the thermocouple and recorded for each test sample and the control.

The foregoing procedurre was repeated for each inhibitor to be evaluated, a control being included with the testing of each inhibitor.

From the recordings the times of occurrence of maximum temperature (exotherm) were averaged for each inhibitor and for the controls. The average times, or raw inhibition times (RIT), are given in Table 1 below. By subtracting the average RIT of the controls from the average RIT of each tested inhibitor the average inhibition time (IT) for each inhibitor was calculated and is also given in Table 1, wherein compounds (A), (B) and (C) are known inhibitors and compounds (1), (2), (3) and (4) are inhibitors according to the present invention.

TABLE 1

| Inhibitor | | Concentration | RIT (hrs) | IT (hrs) |
|---|---|---|---|---|
| | Uninhibited (control) | 0 | 12.2 | 0.0 |
| (A) | Hydroquinone | 10 ppm | 34.2 | 21.9 |
| (B) | 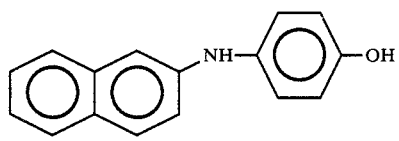 | 10 ppm | 37.1 | 24.9 |
| (C) | diphenylamine | 10 ppm | 21.0 | 8.8 |
| (1) | 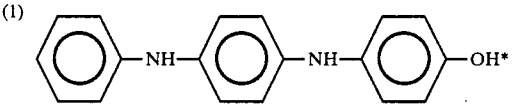 | 10 ppm | 80.1 | 67.9 |

TABLE 1-continued

| Inhibitor | Concentration | RIT (hrs) | IT (hrs) |
|---|---|---|---|
| (2) 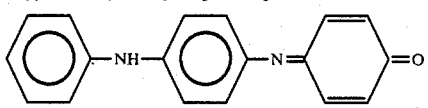 | 10 ppm | 40.1 | 27.9 |
| (3) ![structure] | 10 ppm | 50.4 | 38.2 |
| (4) ![structure] | 10 ppm | 154.0 | 141.8 |

*Approximately 5%, by weight, being in oxidized form having the formula

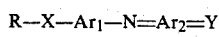

Distillation Testing

A 500 ml resin flask, equipped with a 5-plate Oldershaw column, a multi-ratio distillation head, a high efficiency brine-cooled condenser, a mechanical stirrer, a heating mantle slaved to a constant temperature controller and vacuum equipment was charged with 250 ml of pre-distilled (inhibitor-free) methyl methacrylate monomer and an amount of inhibitor (1) identified in Table 1 to give a concentration of 0.001%, by weight. The monomer was then distilled under vacuum at a temperature of 78° C. and a reflux ratio of 5:1 until no further distillate collected in the receiver. A sample of the collected distillate was then assayed spectrophotometrically at 329 nm to an accuracy of about 0.2 ppm.

The foregoing was repeated two more times with fresh charges of methyl methacrylate and the results were averaged, giving the following results:

% Monomer recovered by distillation—92.4
% Monomer lost to equipment—1.3
% Pot residue—6.3
Distillation Time (in minutes)—295
% Inhibitor co-distilled—0

Under otherwise identical conditions a sample of inhibitor-free methyl methacrylate showed polymerization after one hour to an extent requiring discontinuation of the distillation.

The inhibitors according to this invention have been defined above by formulae which represent their reduced forms. However, as indicated for compound (1) in Table 1, many of these compounds may be present in minor proportions in their corresponding oxidized forms. It has been determined that for compound (1) the oxidized form, per se, does have polymerization inhibiting activity but that is lower than that of the form corresponding to formula (I). Accordingly, the amounts of compound of formula (I) specified herein are intended to include the optional presence of a minor proportion, up to 20% of the total weight of the inhibitor, of the oxidized form, i.e. of the formula (II)

$$R-X-Ar_1-N=Ar_2=Y \qquad (II)$$

wherein $Ar_1$, $Ar_2$, R, X and Y are as defined above.

We claim:
1. A composition comprising a mixture of
   (A) a polymerizable ethylenically unsaturated monomer selected from the group consisting of unsaturated carboxylic acids and the esters, anhydrides, amides, halides and nitriles thereof, vinyl halides, vinyl acetate, vinyl alcohol and aromatic vinyl compounds and
   (B) an amount sufficient to inhibit polymerization of said monomer of a compound or mixture of compounds of formula (I)

$$R-X-Ar_1-NH-Ar_2-Y-H \qquad (I)$$

wherein
   $Ar_1$ and $Ar_2$ are, independently, substituted or unsubstituted phenylene, naphthylene, anthrylene or phenanthrylene,
   X and Y, independently, are —NH—, —S— or —O—,
   R is hydrogen; substituted or unsubstituted $C_{1-10}$ alkyl; substituted or unsubstituted $C_{5-10}$ cycloalkyl; substituted or unsubstituted phenyl, naphthyl, anthryl or phenanthryl; substituted or unsubstituted phenyl $C_{1-10}$ alkyl or naphthyl $C_{1-10}$ alkyl; or substituted or unsubstituted phenyl $C_{5-10}$ cycloalkyl or naphthyl $C_{5-10}$ cycloalkyl;
   and any substituent on $Ar_1$, $Ar_2$ or R is $C_{1-10}$ alkyl, phenyl, naphthyl, phenyl $C_{1-10}$ alkyl, naphthyl $C_{1-10}$ alkyl, $C_{1-10}$ alkoxy, hydroxy, $C_{1-10}$ alkylamino, amino, thiol, $C_{1-10}$ alkylthio, $C_{5-10}$ cycloalkyl, $C_{5-10}$ cycloalkyloxy or $C_{5-10}$ cycloalkylamino.

2. A composition according to claim 1 wherein, in formula (I), any substituent on $Ar_1$, $Ar_2$ or R is, independently, $C_{1-4}$ alkyl, phenyl, naphthyl, phenyl $C_{1-4}$ alkyl, naphthyl $C_{1-4}$ alkyl, $C_{1-4}$ alkoxy, hydroxy, $C_{1-4}$ alkylamino, amino, thiol, $C_{1-4}$ alkylthio, $C_{5-8}$ cycloalkyl, $C_{5-8}$ cycloalkyloxy or $C_{5-8}$ cycloalkylamino.

3. A composition according to claim 1 wherein $Ar_1$ and $Ar_2$ are, independently, substituted or unsubstituted phenylene or naphthylene.

4. A composition according to claim 1 wherein X and Y are, independently, —NH— or —O—.

5. A composition according to claim 2 wherein at least one of X and Y is —NH— and the other is —NH— or —O—.

6. A composition according to claim 5 wherein $Ar_1$ and $Ar_2$ are, independently, substituted or unsubstituted phenylene.

7. A composition according to claim 1 wherein the compound of formula (I) is one of the formula (I'a)

$$R_a-NH-Ar_1'-NH-Ar_2'-Y'-H \qquad (I'a)$$

wherein
$Ar_1'$ and $Ar_2'$ are, independently, substituted or unsubstituted phenylene or naphthylene,
Y' is —NH— or —O—, and
$R_a$ is substituted or unsubstituted phenyl.

8. A composition according to claim 1 wherein the compound of formula (I) is of the formula (I'b)

$$H_2N-Ar_1'-NH-Ar_2'-Y'-H \qquad (I'b)$$

wherein
$Ar_1'$ and $Ar_2'$ are independently, substituted or unsubstituted phenylene or naphthylene and
Y' is —NH— or —O—.

9. A composition according to claim 7, wherein the compound of formula (I'a) is of the formula

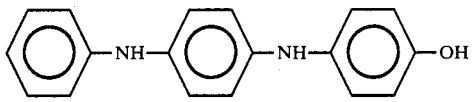

10. A composition according to claim 1 wherein the polymerizable ethylenically unsaturated monomer is a $C_{3-18}$ mono- di- or tricarboxylic acid or anhydride, amide, nitrile, halide or $C_{1-18}$ alkyl or alkenyl ester thereof or a vinyl halide, vinyl acetate, vinyl alcohol or aromatic vinyl compound.

11. A composition according to claim 1 wherein the polymerizable ethylenically unsaturated monomer is acrylic or methacrylic acid or an anhydride, chloride or $C_{1-8}$ alkyl ester thereof.

12. A composition according to calim 3 wherein $Ar_1$ and $Ar_2$ are, independently, phenylene or mono- or di-$C_{1-4}$ alkylphenylene.

13. A composition according to claim 6 wherein $Ar_1$ and $Ar_2$ are, independently, phenylene or mono- or di-$C_{1-4}$ alkylphenylene.

14. A composition according to claim 7 wherein $Ar_1'$ and $Ar_2'$ are, independently, phenylene or mono- or di-$C_{1-4}$ alkylphenylene.

15. A composition according to claim 8 wherein $Ar_1'$ and $Ar_2'$ are, independently, phenylene or mono- or di-$C_{1-4}$ alkylphenylene.

16. A composition according to claim 2 wherein the polymerizable ethylenically unsaturated monomer is a $C_{3-18}$ mono-, di- or tricarboxylic acid or anhydride, amide, halide or $C_{1-18}$ alkyl or alkenyl ester thereof or a vinyl halide, vinyl acetate, vinyl alcohol, styrene, alpha-methyl styrene, vinyl toluene or vinyl naphthalene.

17. A composition according to claim 9 wherein the polymerizable ethylenically unsaturated monomer is selected from the group consisting of acrylic and methacrylic acids and their anhydrides, chlorides and $C_{1-8}$ alkyl esters and styrene.

18. A composition according to claim 3 wherein the polymerizable ethylenically unsaturated monomer is selected from the group consisting of acrylic and methacrylic acids and their anhydrides, chlorides and $C_{1-8}$ alkyl esters and styrene.

19. A composition according to claim 14 wherein the polymerizable ethylenically unsaturated monomer is selected from the group consisting of acrylic and methacrylic acids and their anhydrides, chlorides and $C_{1-8}$ alkyl esters and styrene.

20. A composition according to claim 15 wherein the polymerizable ethylenically unsaturated monomer is selected from the group consisting of acrylic and methacrylic acids and their anhydrides, chlorides and $C_{1-8}$ alkyl esters and styrene.

21. A composition according to claim 18 containing 0.001 to 5%, by weight, compound of formula (I), based on the weight of monomer.

22. A composition comprising a mixture of
(A) a polymerizable ethylenically unsaturated monomer selected from the group consisting of unsaturated carboxylic acids and the esters, anhydrides, amides, halides and nitriles thereof, vinyl halides, vinyl acetate, vinyl alcohol and aromatic vinyl compounds and
(B) an amount effective to inhibit polymerization of said monomer of a mixture of compounds of formula (I) and of the corresponding oxidized form represented by formula (II)

$$R-X-Ar_1-NH-Ar_2-Y-H \qquad (I)$$

$$R-X-Ar_1-N=Ar_2=Y \qquad (II)$$

wherein
$Ar_1$ and $Ar_2$ are, independently, substituted or unsubstituted phenylene, naphthylene, anthrylene or phenanthrylene,
X and Y, independently, are —NH—, —S— or —O—,
R is hydrogen; substituted or unsubstituted $C_{1-10}$ alkyl; substituted or unsubstituted $C_{5-10}$ cycloalkyl; substituted or unsubstituted phenyl, naphthyl, anthryl or phenanthryl; substituted or unsubstituted phenyl $C_{1-10}$ alkyl or naphthyl $C_{1-10}$ alkyl; or substituted or unsubstituted phenyl $C_{5-10}$ cycloalkyl or naphthyl $C_{5-10}$ cycloalkyl;
and any substituent on $Ar_1$, $Ar_2$ or R is $C_{1-10}$ alkyl, phenyl, naphthyl, phenyl $C_{1-10}$ alkyl, naphthyl $C_{1-10}$ alkyl, $C_{1-10}$ alkoxy, hydroxy, $C_{1-10}$ alkylamino, amino, thiol, $C_{1-10}$ alkylthio, $C_{5-10}$ cycloalkyl, $C_{5-10}$ cycloalkyloxy or $C_{5-10}$ cycloalkylamino, with the proviso that the compound of formula (II) comprises up to 20%, by weight, of the mixture of compounds of formulae (I) and (II).

23. A composition according to claim 10 wherein $Ar_1$ and $Ar_2$ are, independently, substituted or unsubstituted phenylene or naphthylene.

24. A composition according to claim 16 wherein $Ar_1$ and $Ar_2$ are, independently, substituted or unsubstituted phenylene or naphthylene.

25. A composition according to claim 16 containing 0.001 to 5%, by weight, compound of formula (I), based on the weight of monomer.

26. A composition according to claim 22 wherein the polymerizable ethylenically unsaturated monomer is a $C_{3-18}$ mono-, di- or tricarboxylic acid or anhydride, amide, halide or $C_{1-18}$ alkyl or alkenyl ester thereof or a vinyl halide, vinyl acetate, vinyl alcohol, styrene, alpha-methyl styrene, vinyl toluene or vinyl naphthalene.

27. A composition according to claim 24 containing 0.001 to 5%, by weight, compound of formula (I), based on the weight of monomer.

28. A composition according to claim 26 wherein, in the compounds of formulae (I) and (II), Ar$_1$ and Ar$_2$ are, independently, substituted or unsubstituted phenylene or naphthylene, X is —NH— and Y is —O—, and the amount of compounds of formula (I) and (II) is 0.001 to 5%, by weight, based on the weight of monomer.

29. A method for inhibiting polymerization of a polymerizable ethylenically unsaturated monomer selected from the group consisting of unsaturated carboxylic acids and the esters, anhydrides, amides, halides and nitriles thereof, vinyl halides, vinyl acetate, vinyl alcohol and aromatic vinyl compounds which comprises admixing with said monomer a polymerization inhibiting-effective amount of a compound of formula (I) or of a mixture of compounds of formula (I) and of the corresponding oxidized form represented by formula (II)

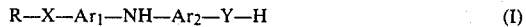

R—X—Ar$_1$—NH—Ar$_2$—Y—H   (I)

R—X—Ar$_1$—N=Ar$_2$=Y   (II)

wherein

Ar$_1$ and Ar$_2$ are, independently, substituted or unsubstituted phenylene, naphthylene, anthrylene or phenanthrylene, X and Y, independently, are —NH—, —S— or —O—, R is hydrogen; substituted or unsubstituted C$_{1-10}$ alkyl; substituted or unsubstituted C$_{5-10}$ cycloalkyl; substituted or unsubstituted phenyl, naphthyl, anthryl or phenanthryl; substituted or unsubstituted phenyl C$_{1-10}$ alkyl or naphthyl C$_{1-10}$ alkyl; or substituted or unsubstituted phenyl C$_{5-10}$ cycloalkyl or naphthyl C$_{5-10}$ cycloalkyl;

and any substituent on Ar$_1$, Ar$_2$ or R is C$_{1-10}$ alkyl, phenyl, naphthyl, phenyl C$_{1-10}$ alkyl, naphthyl C$_{1-10}$ alkyl, C$_{1-10}$ alkoxy, hydroxy, C$_{1-10}$ alkylamino, amino, thiol, C$_{1-10}$ alkylthio, C$_{5-10}$ cycloalkyl, C$_{5-10}$ cycloalkyloxy or C$_{5-10}$ cycloalkylamino, with the proviso that the compound of formula (II) comprises up to 20%, by weight, of the mixture of compounds of formulae (I) and (II).

30. A method according to claim 29 which comprises admixing with the monomer a polymerization inhibiting-effective amount of a compound of formula (I).

31. A method according to claim 30 wherein the amount of compound of formula (I) is 0.001 to 5%, by weight, based on the weight of the monomer.

32. A method according to claim 30 which comprises the further step of distilling the monomer following admixture with the compound of formula (I).

33. A method according to claim 29 wherein Ar$_1$ and Ar$_2$ are, independently, substituted or unsubstituted phenylene or naphthylene.

34. A method according to claim 33 wherein R is substituted or unsubstituted phenyl and at least one of X and Y is —NH— and the other is —NH— or —O—.

35. A method according to claim 34 wherein the polymerizable ethlenically unsaturated monomer is a C$_{3-18}$ mono-, di or tricarboxylic acid or anhydride, amide, halide or C$_{1-18}$ alkyl or alkenyl ester thereof or a vinyl halide, vinyl acetate, vinyl alcohol, styrene, alpha-methyl styrene, vinyl toluene or vinyl naphthalene.

36. A method according to claim 35 which comprises the further step of distilling the monomer following addition of the compound of formula (I) or mixture of compounds of formulae (I) and (II).

37. A method according to claim 35 wherein the compound of formula (I) or mixture of compounds of formulae (I) and (II) is dissolved in an inert solvent prior to being added to the monomer.

38. A method according to claim 36 wherein the compound of formula (I) or mixture of compounds of formula (I) and (II) is dissolved in an inert solvent prior to being added to the monomer.

* * * * *